United States Patent [19]

Burdick et al.

[11] Patent Number: 4,495,402
[45] Date of Patent: Jan. 22, 1985

[54] WARMER FOR TEMPERATURE CONDITIONING WET DRESSINGS AND OTHER ARTICLES

[75] Inventors: Thomas H. Burdick, Deerfield; Alfred Vasconcellos, Crystal Lake; William G. Whitney, Evanston, all of Ill.

[73] Assignee: W. G. Whitney Corporation, Glenview, Ill.

[21] Appl. No.: 307,954

[22] Filed: Oct. 2, 1981

[51] Int. Cl.³ .................... B65D 83/08; H05B 3/20
[52] U.S. Cl. ........................ 219/214; 219/481; 219/494; 219/510; 219/521; 221/146; 221/150 A
[58] Field of Search ............... 219/385, 386, 387, 214, 219/391, 412–414, 527, 481, 482, 510, 516, 506, 497, 521; 604/289, 291, 304; 221/150 A, 150 HC, 150 R, 146, 56

[56] References Cited

U.S. PATENT DOCUMENTS

| 1,659,719 | 2/1928 | Blake | 219/385 |
| 1,941,310 | 12/1933 | Lines | 219/385 |
| 1,989,381 | 1/1935 | Samson | 221/56 |
| 2,211,520 | 8/1940 | Smith | 219/481 |
| 2,502,519 | 4/1950 | Grey | 219/358 |
| 2,686,250 | 8/1954 | Schroeder | 219/510 |
| 2,813,963 | 11/1957 | Lennox | 219/449 |
| 2,840,679 | 6/1958 | Hart | 219/510 |
| 2,908,791 | 10/1959 | Torino et al. | 219/214 |
| 3,020,380 | 2/1962 | Carissimi | 219/494 |
| 3,030,483 | 4/1962 | Rudolph et al. | 219/214 |
| 3,180,247 | 4/1965 | Hill | 221/150 A |
| 3,369,105 | 2/1968 | Wheeler | 219/441 |
| 3,395,318 | 7/1968 | Laermer et al. | 361/404 |
| 3,484,858 | 12/1969 | Jordan et al. | 219/413 |
| 3,710,076 | 1/1973 | Frazier | 219/358 |
| 4,084,080 | 4/1978 | McMahan | 219/386 |
| 4,163,896 | 8/1979 | McAvinn et al. | 219/521 |
| 4,192,992 | 3/1980 | Stevens et al. | 219/328 |
| 4,289,253 | 9/1981 | Andersson | 221/150 A |
| 4,322,594 | 3/1982 | Brisson | 219/497 |
| 4,329,568 | 5/1982 | Rocher et al. | 219/497 |
| 4,331,859 | 5/1982 | Thomas et al. | 219/521 |
| 4,405,855 | 9/1983 | Kolle et al. | 219/501 |

FOREIGN PATENT DOCUMENTS 53-139078 12/1978 Japan .................... 219/481

Primary Examiner—Roy N. Envall, Jr.
Assistant Examiner—Geoffrey S. Evans
Attorney, Agent, or Firm—Hill, Van Santen, Steadman & Simpson

[57] ABSTRACT

A warmer for heating wet dressings and other articles disposed in a combined heating and storage compartment in stacked relation insures that a bottommost article about to be dispensed is at a proper temperature so as to avoid burning the patient to whom the article is applied. The articles in stacked relation rest on a thin aluminum plate to which an electrical heater is connected for supplying thermal energy thereto, the plate having a center aperture forming a thermal island in which a first thermal sensor is disposed which projects into the compartment in contact with the bottommost one of the articles therein. A circuit board has control circuitry for the heater thereon and is disposed beneath the plate so as to simultaneously function as a stiffener for the plate. The control circuitry is connected to the first sensor as well as to a second thermal sensor which is directly responsive to the temperature of the heater. The control circuitry automatically limits the thermal energy supplied to the compartment as a function of the sensed temperature of the first and second thermal sensors for bringing the temperature of the bottommost article to a selected level and maintaining the temperature of that article at the selected level.

14 Claims, 5 Drawing Figures

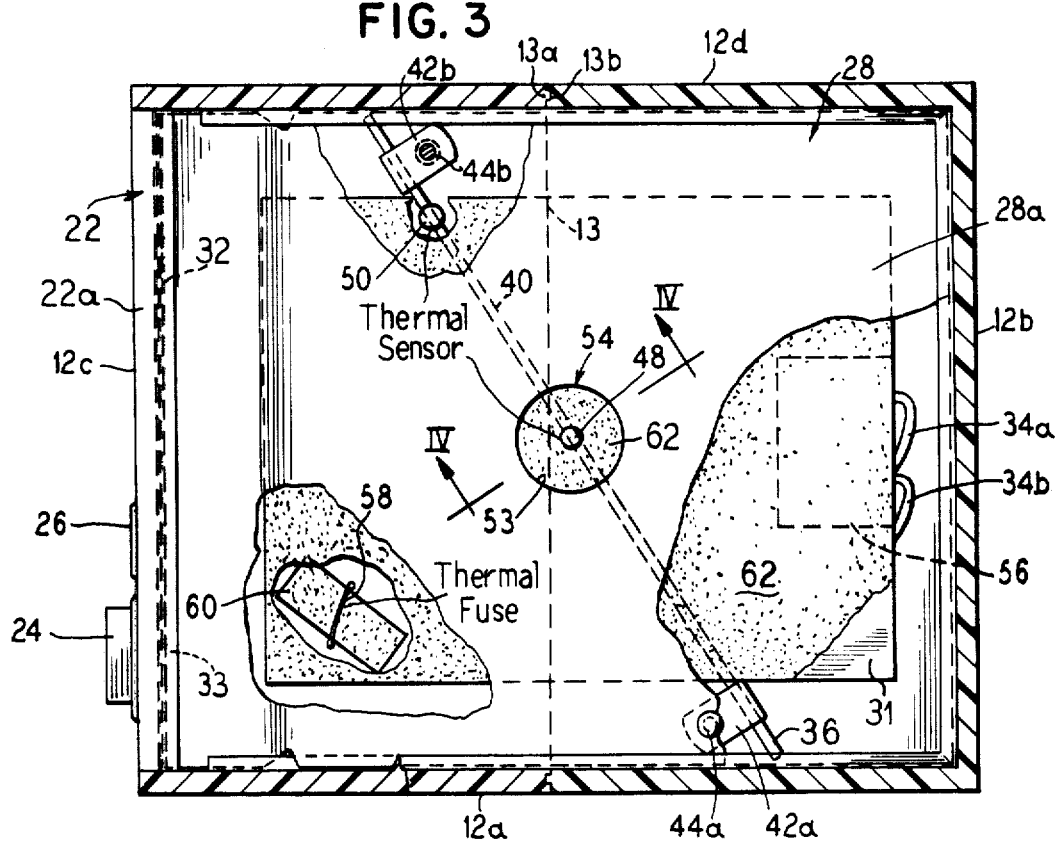
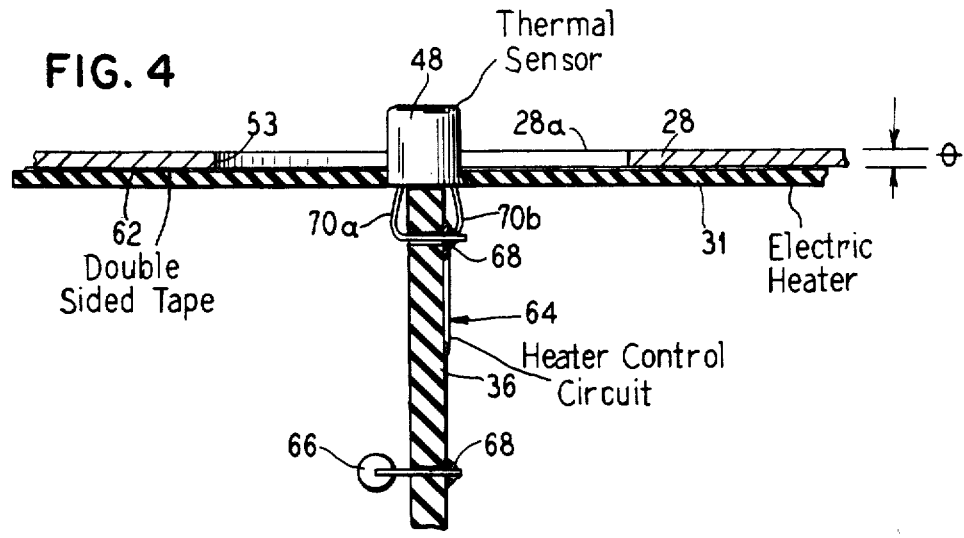

WARMER FOR TEMPERATURE CONDITIONING WET DRESSINGS AND OTHER ARTICLES

BACKGROUND OF THE INVENTION

1. Field of the Invention

This invention relates to a method and means for warming to a predetermined temperature, a wet dressing pack and other medicaments of the type used by health care providers and specifically to a device for warming and maintaining the wet dressing pack at a temperature below that which might cause discomfort or injury to the skin of a patient.

2. Prior Art

Conventional means for heating wet dressing packs employ a timed heat lamp which heat the dressings by radiation for a selected period of time. However, such devices provide no means for detecting and/or controlling the temperature of the wet dressing packs. Consequently, the longer the wet dressing packs are left under the exposure of the heat lamp, the hotter they become, sometimes resulting in the production of steam within the dressing packs. This presents the danger of overheated dressing packs burning the skin of patients, especially if comatose or sedated.

Further, each time a wet dressing pack is required, the pack is placed under the heat lamp for a certain period of time until the pack reaches an unknown elevated temperature. As soon as the heat lamp is turned off, the wet dressing pack immediately begins to cool down to room temperature. Additionally, if a second wet dressing pack is required and it is placed under the same heat lamp, which was still warm, the time required to heat the second wet dressing pack would be less than that required if the lamp had been cooled to room temperature. Under such conditions, heating a wet dressing pack to a desired temperature by conventional devices is done on a strictly hit or miss trial and error basis.

Other substitute methods such as using hot water, heating pads, chemical hot packs and other devices not originally intended for the purposes of heating wet dressings have also been employed in an attempt to solve the problem in the art with results which were even more unacceptable than those produced from the use of a heat lamp.

SUMMARY OF THE INVENTION

This invention relates to an electrical device to warm a wet dressing pack to a predetermined temperature. The invention consists of an open top container insulated both electrically and thermally by a suitable foam-type material, and having an opening in the front portion thereof so as to provide a means for selectively removing a warm wet dressing pack from a supply in the container. A thin metal plate partitions the lower interior portion of the container into a temperature conditioned storage compartment and a mechanism compartment. The thinness of the metal plate minimizes thermal lag resulting from changes in temperature. A heat pad is affixed to the underside of the metal plate to temperature condition the plate selectively. A circuit board which is mounted to extend vertically and diagonally across the lower compartment of the container and acts as a stiffener for the center portion of the metal plate. The metal plate is capable of supporting up to 10 wet dressing packs laid flat in a stacked arrangement within the upper storage compartment of the container on the metal plate. A first thermal sensor is mounted in the center portion of the metal plate and directly measures the temperature of the wet dressing pack superjacent thereto, but not the metal plate.

A second thermal sensor is mounted on the underside of the metal plate in order to sense the temperature of the heating pad. A thermal fuse is positioned on the underside of the heat pad so as to protect the entire device should the temperature controls fail and the temperature of the heating pad begins to "run away".

Once the temperature of the wet dressing packs reaches the predetermined temperature desired by the user, the temperature of the heating pad is lowered so as to be slightly above the temperature of the thermal island surrounding the first thermal sensor, and which will maintain the final temperature of the dressing pack for an indefinite period of time.

If the bottom wet dressing pack is not immediately used, the packs above the bottom pack will be heated so that more than one pack will reach the desired end temperature. Because of this feature, a user may have several wet dressing packs available at the proper temperature for use, eliminating the time to heat additional packs and making efficient thermal use of the device.

Embodiments of the present invention may be used as a blood bag warmer, I.V. solution warmer, and enteric feeding warmer, and a gel pack warmer.

BRIEF DESCRIPTION OF THE DRAWINGS

FIG. 3 is a top plan view, partially cutaway, of the wet dressing warmer of FIGS. 1 and 2.

FIG. 4 is a fragmentary cross-sectional view on the plane of line IV—IV of FIG. 3.

DESCRIPTION OF THE PREFERRED EMBODIMENTS

While the principles of the present invention find utility in a warmer particularly suited for the health care industry and specifically health care providers such as hospitals, clinics and nursing homes, it will be understood that the arrangement of the present invention might be useable in other combinations as well.

Figure 1:
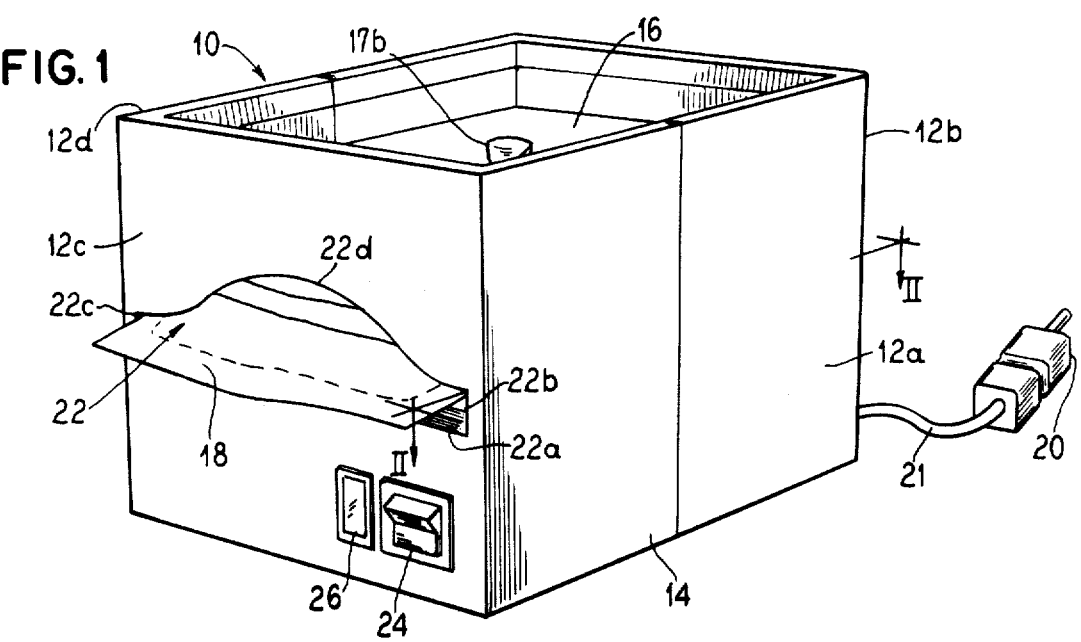
FIG. 1 is a perspective view of a wet dressing warmer in accordance with this invention.

By way of exemplary disclosure of the best mode of practicing the invention, there is shown generally in FIG. 1 a container 10 having a plurality of upstanding sidewalls 12a, 12b, 12c, 12d and a bottom wall 14 generally enclosing an interior compartment bounded by the walls.

The sidewalls 12a-d, inclusive, and the bottom wall 14 are composed of an insulated foam material such as acrylonitrile, butadiene, styrene, but commonly known as ABS, provides both electrical and thermal insulation for the container 10.

The container 10 is preferably formed by molding the ABS material in two modules joined at a parting line 13 and tongued and grooved as at 13b and 13c.

The interior wall surfaces of the walls 12a-d are formed with an internally projecting grooved rib 15 presenting a groove 15a opening into the interior of the container 10 at a median portion thereof. The wall 12c is formed with an opening 22 which is generally rectangular in configuration, i.e., having a horizontal lower edge 22a, two side edges at opposite ends 22b and 22c and an upper arched edge as shown at 22d.

Immediately below the lower edge 22a of the opening 22, there is formed an inwardly projecting ledge 32 on the wall 12c forming an abutment surface and a ledge 33 spaced thereabove and together therewith forming a channel 35.

The opposite wall 12b has a similar construction, for purposes of permitting volume production of stockpiled modules.

Figure 2:
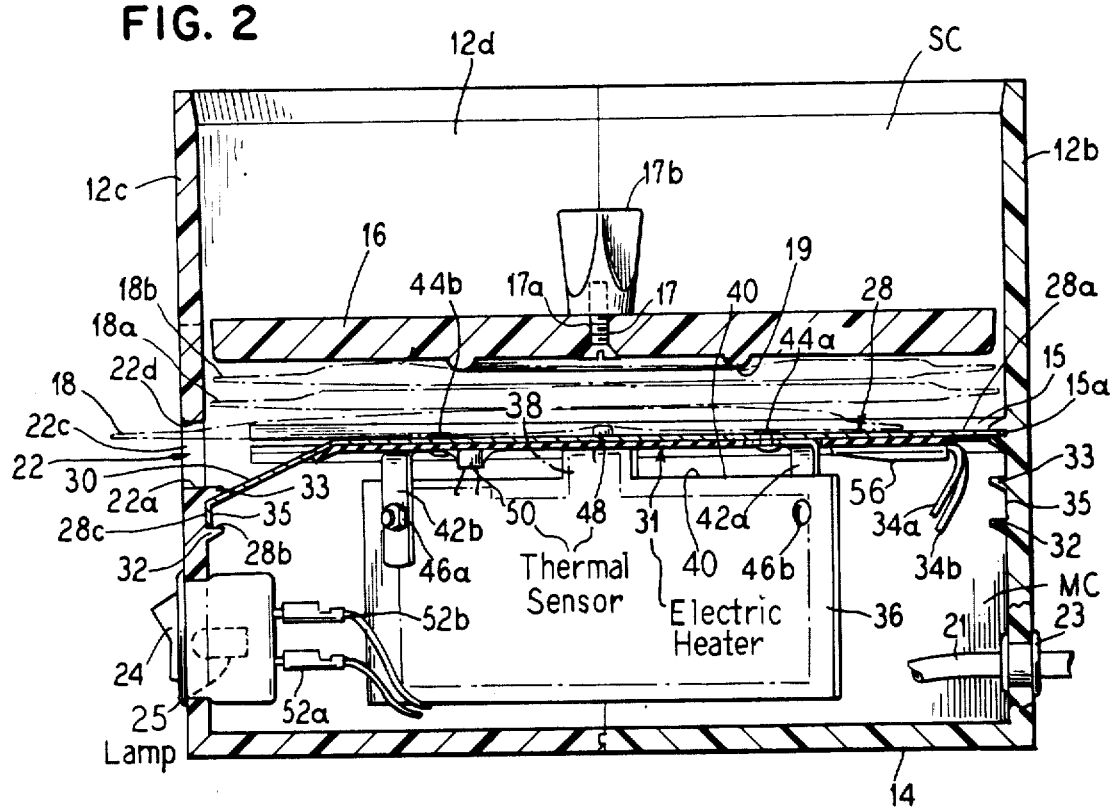
FIG. 2 is a cross-sectional view with parts shown in elevation of the wet dressing warmer taken generally in the plane of line II—II of FIG. 1.

As shown in FIGS. 2 and 3, a thin metal plate 28 is mounted within the container 10 in the groove 15a and is disposed to partition the interior of the container 10 into an upper storage compartment SC and a lower mechanism compartment MC. The thin plate 28 is preferably made of a thermally conductive metal such as aluminum so that it will quickly and efficiently respond to temperature changes induced in it by conduction or radiation. Thus, the plate 28 not only forms a floor for the storage compartment SC, but the plate 28 also functions as a temperature conditioning radiator and forms an upper radiating and support surface 28a for imparting and transmitting thermal energy to the storage compartment SC and the contents thereof.

In order to provide sufficient structural strength while at the same time maintaining the thermal dynamic properties necessary for the proper operation of the unit, we have determined that the optimal thickness of the metal plate 28 must be in the range of from about 0.013 to 0.016 inches, or 0.033 to 0.040 centimeters. This optimal thickness enables the plate 28 to function satisfactorily as a support floor while at the same time functioning as a radiator exhibiting mimimal thermal lag produced as a result of changes in temperature.

In order to provide additional support, the thin plate 28 is shaped to provide an angle support portion 30 which extends downwardly from the level of the main body portion of plate 28 towards the channel 35 on the wall 12c. The outermost edge 28b engages the abutment surface 32 and a depending flange 28c fits in the channel 35.

In order to provide means for warming the metal plate 28 to the desired temperature, heating means 31 are provided including input wires 34a, 34b.

The heating means 31 conveniently constitutes a silicone sheath-type of heating component which is a thin, flat element roughly coextensive in area or slightly smaller than the plate 28 and secured in firm integral assembly on the underside of the plate 28 by means of a pressure-sensitive adhesive which is part of the heating element 31. For example, a unit rated 120 volts, 100 watts will satisfactorily perform in the combination disclosed herein.

The electrical components of the device are powered from any convenient source of electrical energy. There is shown an AC plug 20 of hospital grade, i.e., a grounded plug connected to conductor wires 21 of suitable electrical capacity. A rubber insulating grommet 23 carried in a suitable aperture formed in the wall 12b admits the wires 21 into the interior of the container 10.

An on-off power switch 24 is affixed to the sidewall 12c in an accessible location on the outside of the container. The switch 24 has an indicator light 25 which indicates when the unit is energized. A ready light 26 is mounted adjacent thereto on the sidewall 12c to indicate when the contents of the container are at the desired temperature.

In accordance with this invention, the thin plate 28 is reinforced and strengthened and the electrical control of the device is accomplished by use of a circuit board 36 disposed in right angle relation to the plate 28 and extending at a bias angle to approximately intersect the center of the plate 28.

Since the plate 28 forms the floor of the storage compartment SC, a plurality of wet dressing packs 18 are loaded into the storage compartment SC and are supported on the plate 28, and are selectively removed via the opening 22.

A cover 16 sized and shaped to be complementary with the open top of the container and made of the same ABS material nests within the compartment SC and engages against the top of the packs.

An annular ridge 19 is integrally formed on the bottom surface of the cover 16. A central aperture 17 passes a screw fastener 17a which secures a knob or handle 17b on the upper side of the cover 16.

The circuit board 36 has an elevated plateau portion 38 along one longitudinal edge 40 which is affixed to the metal plate 28 by means of a pair of L-shaped brackets 42a, 42b affixed to one end of the metal plate 28 by means of a pair of rivets 44a, 44b, and at the other end, to the circuit board 36 by means of a pair of nuts and bolts 46a, 46b.

A first thermal sensor 48 is affixed to the elevated plateau portion 38 of the circuit board 36 and positioned so as to sense the temperature of the bottom wet dressing pack 18, i.e., it projects upwardly into the storage compartment SC for engagement with the lowermost dressing pack 18.

A second thermal sensor 50 is affixed to the longitudinal edge 40 of the circuit board 36 and directly abuts the heating pad 31 in order to sense the temperature of the heating pad 31. When the first thermal sensor 48 senses that the wet dressing pack 18 has reached a predetermined desired temperature, the ready light 26 will be energized, indicating to the user that the wet dressing pack is at the desired temperature and ready for use. At this point, the bottom wet dressing pack 18 is maintained at the desired temperature by switching control of the heating element 31 to the thermal sensor 50.

Such thermal operating conditions will be maintained as long as power is supplied to the unit, or until the bottom wet dressing pack 18 is removed from the container 10 and the thermal sensor 48 detects a temperature below the desired end temperature. If a second wet dressing pack 18a requires warming, the ready light 26 will switch off, and a higher boost temperature will be maintained in the heating pad 31 automatically until the second wet dressing pack 18a reaches the desired temperature. At that point, the process will repeat itself. Subsequent wet dressing packs 18a, 18b positioned above the bottom wet dressing pack 18 will be partially heated by means of the thermal energy transmitted into the compartment SC or via the subjacent dressing pack and, therefore, will require less time to be heated to the desired temperature.

A pair of push-on plugs 52a, 52b provide the connecting means whereby the entire thermal control process for the wet dressing packs 18 may be engaged by means of the on-off power switch 24.

FIG. 3 shows how a thermal island 54 is formed around the thermal sensor 48 by forming circular aperture 53 in the thin plate 28 through which the sensor 48 extends. The thermal island 54 insures that the temperature maintained on the metal plate 28 will not affect the readings of the thermal sensor 48. This is to insure that the thermal sensor 48 only senses and reacts to the temperature of the wet dressing packs 18 positioned adjacent thereto. The input wires 34a, 34b are secured to the heat pad 31 by means of a patch 56.

A thermal fuse 58 is mounted to the heating pad 31 at a location remote from the sensors 48 and 50 by means of a retainer strip 60. The thermal fuse 58 acts to protect the entire system should the normal temperature controls fail and the temperature of the heat pad 31 begins to increase to an unacceptable level.

As seen in FIG. 4, a double sided adhesive strip 62 is used to secure the metal plate 28 to the heating pad 31.

An electronic control circuit means 64 is shown attached to the circuit board 36. A resistor 66 is shown affixed to the circuit board by means of solder 68. The thermal sensor 48 is also affixed to the circuit board 28 by means of a plurality of arms 70a, 70b which are soldered to the circuit board 36.

Figure 5:
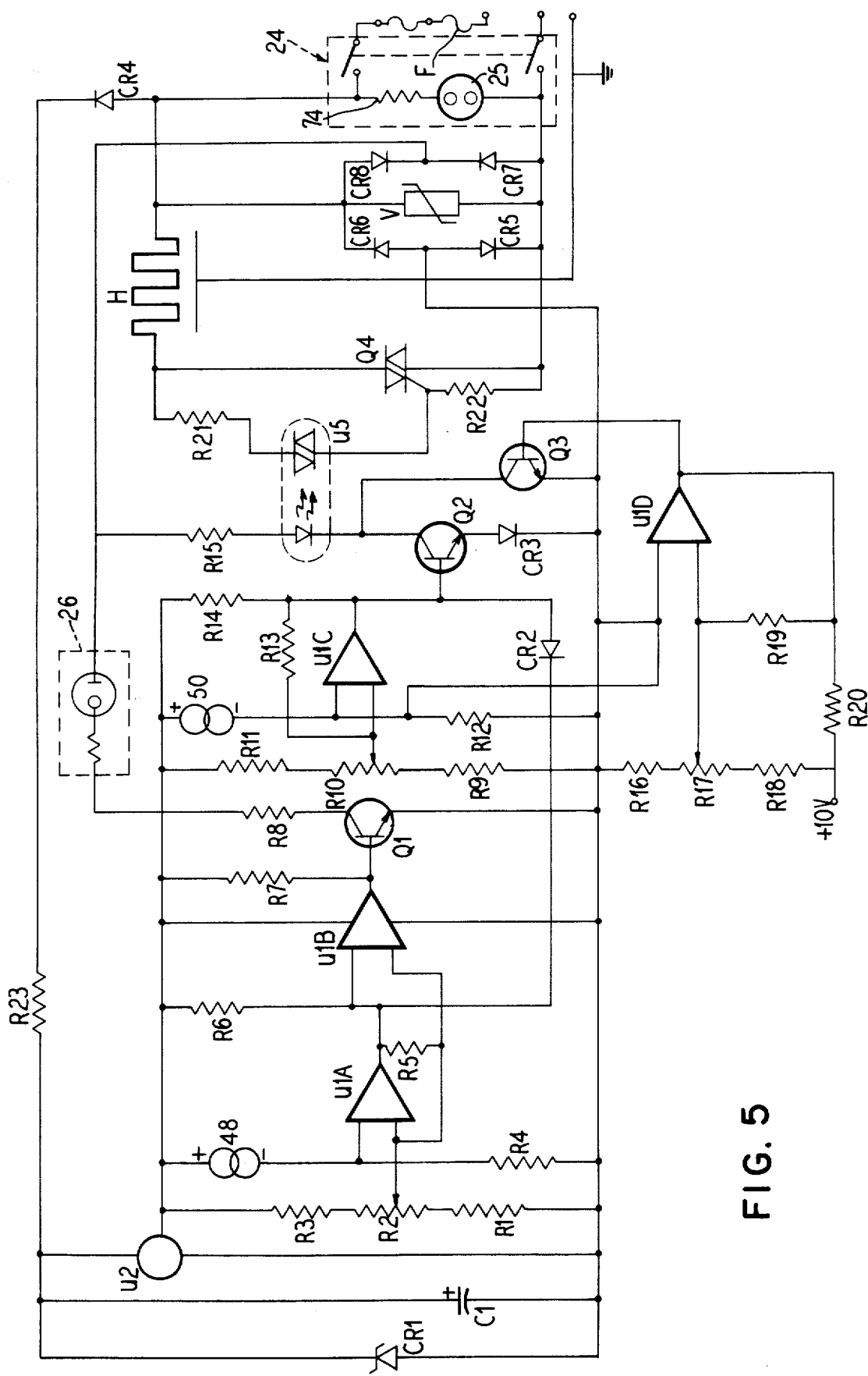
FIG. 5 is a schematic circuit diagram for the thermal control circuitry of the wet dressing warmer.

FIG. 5 shows schematically the components of the circuit means 64 for the wet dressing warmer. The on-off power switch 24 is a double pole, single throw switch containing the integral neon light 25 which illuminates when the switch 24 is in the ON position, and an integral current limiting resistor 74. An exemplary embodiment of the on-off switch 24 is Carling Switch, Model No. LTG70411-TWBN. A noise-suppressing element V is used to reduce voltage fluctuations occurring in the line voltage. The wet dressing warmer is designed to make use of any standard 110 volt AC current.

A heating element H in the heating pad 31 is directly controlled by a triac Q4, which is in turn triggered by a photo-triac U5. The heater H will be in the ON mode whenever current is conducted through transistors Q2 or Q3, which in turn will result in current flow through resistor R15 and the photodiode of U5.

The temperature of the metal plate 28, which is maintained at a relatively constant temperature when the power switch 24 is in the ON mode, is monitored by the temperature sensor 50 which supplies a current in proportion to the sensed temperature. The minimum threshold voltage needed to maintain the minimum temperature for the metal plate 28 is determined by the setting of a potentiometer R17 which is connected across a 10V supply with resistors R16 and R18. A comparator U1D, having its first input terminal connected to potentiometer R17 and a second input terminal connected to thermal sensor 50, is used to direct current to the base of a transistor Q3 connected in series to the output terminal of U1D so as to detect and maintain the required voltage needed to keep the metal plate at the minimum temperature. A resistor R19, connected in parallel with potentiometer R17 and to the supply through R20, determines the hysteresis which results from the temperature differential. Whenever the temperature of the metal plate 28 is above the minimum, the output of U1D will be low with the result that no current will flow through transistor Q3 since the resulting output voltage of U1D will be below the base voltage required to cause transistor Q3 to conduct. No heating action will result via this path under these conditions.

When the wet dressing pack 18 is required to be warmed, the required heating action is provided by the current path through comparators U1A and U1C and transistor Q2. One input terminal of U1A is connected in series to a second potentiometer R2 also including R1 and R3, while the second input terminal is connected to the first thermal sensor 48 which provides a source of current. The first input terminal of U1C is connected in series to a third potentiometer R10, also including R9 and R11, while the second output terminal is connected to the second thermal sensor 50 which provides a source of current. The output of U1A is connected in series to resistor R14 through R6, and R14 and the output U1C are connected to the base of a transistor Q2.

When the threshold voltage of comparators U1A and U1C is reached so that both are in a high output state, current is conducted through transistor Q2 via resistor R14, thus energizing the photo-triac U5 and the heater H. When the metal plate 28 has reached its maximum temperature which is determined by the setting of the third potentiometer R10, the output of comparator U1C is reduced, with its output terminal supplying current which in turn establishes the base of transistor Q2 at about 0.1 volts, which is below the 1.2 turn-on voltage of Q2, with the corresponding result that no current is being conducted through resistor R14.

The temperature of the wet dressing packs 18 is detected by thermal sensor 48. When this temperature reaches a temperature at which the wet dressing pack 18 may be comfortably and safely applied to the skin of a patient, the output of comparator U1A is reduced to approximately 0.1 volts which sets the base of transistor Q2 at below 0.1 volts which is below the 1.2 volt turn-on voltage of transistor Q2 with the result that no current will flow.

It should be noted that because of the wired OR configuration of comparators U1A and U1C, the heater H will not attempt to reach its maximum temperature when the sensor 48 in the thermal island 54 is above its ready temperature.

Comparator U1B, having one of its inputs connected in parallel to potentiometer R2 and its other input connected to the output of U1A, is connected in series and functions with transistor Q1 for energizing the ready light 26 whenever comparator U1A indicates that the thermal sensor 48 is above the point determined by the potentiometer setting.

Rectifiers CR5, CR6, CR7, and CR8 full wave rectify AC voltage for the "turn-on" paths of Q2 and Q3 in order that the heating will occur over both half-cycles of the AC line. Rectifier CR4, resistor R23, and zener diode CR1 limit the input voltage for reference voltage source U2 to about 20 volts DC. The source U2 has a 10.0 volt stable output reference voltage which furnishes the reference for the various temperature control elements in the circuit.

The comparators U1A, U1B, U1C and U1D may be contained in a single dual-in-line package U1 with the outputs of U1 being the collectors of NPN transistors with grounded emitters.

Although the values of the components shown in FIG. 5 may be selected to meet individual circuit requirements in a manner known to those skilled in the art without departing from the inventive concept disclosed herein, an exemplary embodiment of the circuit of FIG. 5 can be realized by using components having the following values:

| | |
|---|---|
| R1, R3, R9, R11, R16, R18 | 33KΩ ± 5% |
| R4, R6, R7, R12, R14, R20 | 16KΩ ± 5% |
| R5, R13, R14 | 10 MΩ ± 10% |

| -continued | |
|---|---|
| R15 | 12KΩ ± 10% |
| R8, R21 | 100Ω ± 10% |
| R22 | 22Ω ± 10% |
| R23 | 5.6KΩ ± 10% |
| R2, R10, R17 | Piher PT 101 H 5KΩ ± 20% |
| C1 | 100μ ± 20%/25 VDC |
| CR1 | IN 968 20 V ± 20% |
| CR2, CR3 | IN 4148 |
| CR4, CR5, CR6, CR7, CR8 | IN 4004 |
| Q1, Q2, Q3 | IN PS - A42 |
| Q4 | TECCOR Q 4001 L4 |
| U1 | MC 3302 (Motorola) |
| U2 | Analog Devices AD5813 |
| 48, 50 | Analog Devices AD590IH |
| U5 | MOC 3011 (Motorola) |
| V | V130LA 29(B) (General Electric) |
| Power Switch (24) | Carling SW LTG 2041-TWBN |
| Ready Light (26) | Sorenson LTC 2LRN1 |

Although the above-described apparatus and method of operation have been explained in the context of a wet-dressing warmer, the method and apparatus have utility in warming other products such as bloodbags, I.V. solutions, and gel packs to name a few.

Although modifications and changes may be suggested by those skilled in the art, it is the intention of the inventors to embody within the patent warranted hereon all changes and modifications as reasonably and properly come within the scope of their contribution to the art.

We claim as our invention:

1. A warmer for articles disposed in stacked relation comprising,
  a container made of thermal and electrical insulating material and forming an inner compartment,
  a thin aluminum plate in the range of from about 0.013 to 0.016 inches in thickness disposed horizontally in said inner compartment to partition the compartment into an upper combined storage and heating compartment for receiving said articles in stacked relation to be warmed, and a lower mechanism compartment,
  electrical heating means on the lower side of said thin aluminum plate to deliver thermal energy thereto,
  said thin aluminum plate having a center aperture forming a thermal island in which is disposed in thermal isolation a first sensing means projecting into said combined heating and storage compartment for engaging a bottommost one of said articles in stacked relation in said combined heating and storage compartment for sensing the temperature of said bottommost article,
  and circuit control means connected to said heating means including said first sensing means and further including a second sensing means directly responsive to the temperature of such said heating means, and including means for selectively limiting the thermal input delivered to the storage compartment as a function of the sensed temperature of said first and second sensing means for bringing the temperature of said bottommost article to a selected level and maintaining said temperature of said bottommost article at said selected level.

2. An electrical warming device comprising:
  an insulated combined storage and heating container;
  a thin metallic plate positioned within said insulated storage and heating container and capable of supporting at least two elements to be warmed, said elements being placed in a stacked arrangement on said thin metallic plate;
  a means for dispensing a bottom one of said elements adjacent to said thin metallic plate;
  a first thermal sensor mounted to said thin metallic plate for contact with said bottom one of said elements, said first thermal sensor being thermally isolated from said thin metallic plate for monitoring the temperature of said bottom element placed on said thin metallic plate;
  a second thermal sensor mounted to said thin metallic plate and positioned for directly monitoring the temperature of said thin metallic plate;
  heating means for increasing the temperature of said thin metallic plate for increasing the temperature of said bottom element to a predetermined level;
  control means connected to said heating means and to said first and second thermal sensors and being responsive to signals received from said first and second thermal sensors for automatically reducing and maintaining the temperature of said thin metallic plate upon the temperature of said bottom element reaching a selected temperature, such that said thin metallic plate and said bottom element are maintained at a substantially constant temperature, and for automatically disengaging said heating means when a selected maximum temperature for said thin metallic plate is exceeded.

3. An electrical warming device comprising:
  an insulated container;
  a non-self-supporting metallic plate positioned within said insulated container for supporting at least two elements to be warmed in a stacked arrangement on said metallic plate;
  heating means positioned beneath said metallic plate for converting electric current into heat for warming said metallic plate;
  a means for dispensing a bottom one of said elements in said stacked arrangement adjacent to said plate;
  a circuit board structurally connected beneath said metallic plate for stiffening said metallic plate;
  a first thermal sensor mounted to said metallic plate in thermal isolation therefrom in contact with said bottom element for monitoring the temperature of said bottom element on said metallic plate;
  a second thermal sensor mounted to said metallic plate for directly monitoring the temperature of said metallic plate;
  control means carried on said circuit board connected to said first and second thermal sensors and to said heating means for automatically reducing and maintaining the temperature of said metallic plate upon the temperature of said bottom element reaching a selected temperature in response to a signal from said first sensor, such that said metallic plate and said bottom element are maintained at a substantially constant temperature and for automatically disengaging said heating means when a selected maximum temperature for said metallic plate is exceeded in response to a signal from said second sensor.

4. The electrical warming device of claim 3 in which said insulating container consists of acrylonitrile, butadiene, styrene for both thermal and electrical insulation.

5. The electrical warming device of claim 3 in which said metal plate has a thickness in the range of 0.013 to 0.016 inches.

6. The electrical warming device of claim 3 in which said control means includes a thermal fuse for automatically disengaging said heating means.

7. The electrical warming device of claim 3 in which said circuit board is mounted vertically and diagonally to the underside of said metallic plate.

8. The electrical warming device of claim 3 in which said heating means is an electric heating pad positioned below and abutting said metal plate.

9. The electrical warming device of claim 3 in which said first thermal sensor is positioned within a thermal island formed on said metal plate for insuring accurate temperature measurements of said bottom element.

10. The electrical warming device of claim 3 in which said elements are wet dressing packs.

11. In a wet dressing warmer having a metal plate, an apparatus for controlling the temperature of said metal plate and a wet dressing pack laid directly on top of said metal plate, said apparatus comprising:
- an electric heating pad connected to a power source, said heating pad affixed to the underside of said metal plate;
- a first thermal sensor mounted to and protruding from said metal plate and thermally isolated therefrom for direct contact with said wet dressing pack;
- a second thermal sensor mounted to and directly abutting said metal plate for measuring the temperature of said metal plate;
- control means connected to said heating pad and responsive to said first and second thermal sensors for increasing the temperature of said metal plate for increasing the temperature of said wet dressing pack to a selected level; and
- control means connected to said heating pad and responsive to said first and second thermal sensors for reducing and maintaining the temperature of said metal plate for maintaining the temperatures of said metal plate and said wet dressing packs at a same selected level.

12. The apparatus of claim 11 further comprising a rectifier bridge for supplying full wave rectified AC voltage from said power source to said heating pad.

13. The apparatus of claim 11 which said control means for increasing the temperature of said metal plate comprises:
- a first comparator having a first input connected to said first thermal sensor and a second input connected to a reference voltage through a first potentiometer for setting a threshold voltage for said first comparator;
- a second comparator having a first input connected to said second thermal sensor and a second input connected to said reference voltage through a second potentiometer for setting a threshold voltage for said second comparator;
- a transistor interconnected between said heating pad and said power source having a base electrode connected to the output of said first and second comparators, said comparators supplying a signal to said base electrode for permitting said transistor to supply power from said power source to said heating pad when the threshold voltages for said first comparator and for said second comparator are simultaneously exceeded.

14. The apparatus of claim 11 in which said control means for maintaining said metal plate at a minimum temperature and said means for reducing and maintaining the temperature of said metal plate comprise:
- a comparator having a first input connected to said second thermal sensor and a second input connected to a reference voltage through a potentiometer for setting a threshold voltage for said comparator; and
- a transistor interconnected between said power source and said heating pad having a base electrode connected to an output of said comparator, said comparator supplying a signal to said base electrode for permitting said transistor to supply power from said power source to said heating pad until said threshold voltage is exceeded.

* * * * *